ic Patent [19] [11] Patent Number: 4,919,145
Marriott [45] Date of Patent: Apr. 24, 1990

[54] METHOD AND APPARATUS FOR SENSING LEAD AND TRANSTHORACIC IMPEDANCES

[75] Inventor: Arthur R. Marriott, Seattle, Wash.

[73] Assignee: Physio-Control Corporation, Redmond, Wash.

[21] Appl. No.: 219,080

[22] Filed: Jul. 13, 1988

[51] Int. Cl.$^5$ ............................................. A61B 5/08
[52] U.S. Cl. .................................. 128/723; 128/734; 128/696
[58] Field of Search ................ 128/696, 671, 734, 782

[56] References Cited

U.S. PATENT DOCUMENTS

| | | | |
|---|---|---|---|
| 3,608,542 | 9/1971 | Pacela | 128/723 |
| 4,141,351 | 2/1979 | James et al. | 128/696 |
| 4,416,288 | 11/1983 | Freeman . | |
| 4,459,993 | 7/1984 | Foreman . | |
| 4,478,223 | 10/1984 | Allor . | |
| 4,527,567 | 7/1985 | Fischler et al. . | |
| 4,565,201 | 1/1986 | Lass . | |
| 4,577,639 | 3/1986 | Simon et al. . | |
| 4,580,575 | 4/1986 | Birnbaum et al. | 128/671 |
| 4,610,254 | 9/1986 | Morgan et al. . | |
| 4,619,265 | 10/1986 | Morgan et al. . | |
| 4,630,204 | 12/1986 | Mortara . | |
| 4,679,144 | 7/1987 | Cox et al. . | |
| 4,785,812 | 11/1988 | Pihl et al. | 128/734 |
| 4,840,182 | 6/1989 | Carlson | 128/734 |

FOREIGN PATENT DOCUMENTS

| | | | |
|---|---|---|---|
| 2515026 | 4/1983 | France | 128/696 |
| 86/03391 | 6/1986 | PCT Int'l Appl. | 128/734 |

Primary Examiner—Ruth S. Smith
Assistant Examiner—John D. Zele
Attorney, Agent, or Firm—Christensen, O'Connor, Johnson & Kindness

[57] ABSTRACT

A method and apparatus for use with medical electrode systems that sense the integrity of lead connections and patient transthoracic impedance is provided. In an ECG electrode application, a carrier circuit (12) produces two carrier signals ($S_{C1}$ and $S_{C2}$) that are out of phase with each other. The $S_{C1}$ signal is applied to an RA lead through a terminating impedance (Z1). The $S_{C2}$ signal is applied to LA, LL and V leads through terminating impedances (Z2, Z3, and Z4). Each of the $S_{C1}$ and $S_{C2}$ carrier signals comprises a lead impedance frequency component ($S_{LI}$) and an impedance respiration frequency component ($S_{IR}$). First stage amplifiers (A1, A2, and A3) located in an ECG preamplifier (13) amplify the difference between a lead voltage on the RA lead ($V_{RA}$) and lead voltages on the LA, LL, and V leads ($V_{LA}$, $V_{LL}$ and $V_V$). High pass filters (F1, F2 and F3) remove patient ECG signals from the outputs of A1, A2 and A3 to produce first stage output voltages ($V_1$, $V_2$ and $V_5$). The $V_1$, $V_2$ and $V_5$ voltages are demodulated by a demodulator circuit (18). Lead impedance demodulators (DM1, DM2 and DM3) are clocked by a lead impedance control signal ($S_A$) that has the same frequency as the $S_{LI}$ component so that the outputs of DM1, DM2 and DM3 are lead impedance-related voltages ($V_{L1}$, $V_{L2}$ and $V_{L5}$). $V_2$ is also demodulated by an impedance respiration demodulator (DM4). DM4 is clocked by an impedance respiration control signal ($S_B$) that has the same frequency as the $S_{IR}$ component so that the output of DM4 is a transthoracic impedance-related voltage $V_T$. $V_T$ is amplified by an operational amplifier (OA10) to produce an impedance respiration-related voltage ($V_R$). The ECG preamplifier (13) and the demodulator circuit (18) include fast DC restoration circuits (66, 68, 70 and 71) that use switched capacitor integrators (76) to restore ECG outputs ($V_{E1}$, $V_{E2}$, and $V_{E5}$) and the $V_R$ voltage to nominal values when a DC offset has occurred.

18 Claims, 5 Drawing Sheets fig.1.

METHOD AND APPARATUS FOR SENSING LEAD AND TRANSTHORACIC IMPEDANCES

TECHNICAL FIELD

This invention relates generally to medical diagnostic and therapeutic apparatus employing electrodes applied to the skin of a patient and, more particularly, to apparatus for sensing the integrity of lead connections and patient transthoracic impedance.

BACKGROUND OF THE INVENTION

As the use of multiple-electrode systems has increased, so has the need to continuously sense the condition of leads which connect a patient to a piece of equipment, such as a medical diagnostic or therapeutic apparatus. A lead, as discussed herein, comprises an electrode and a conductor connecting the electrode to the piece of equipment. The loss of electrical continuity in the lead between a patient and a diagnostic or therapeutic apparatus usually occurs as an electrode becomes separated from a patient's skin, and is referred to as a leads-off condition. Such a condition in a multiple-electrode system will cause the diagnostic or therapeutic apparatus to receive erroneous and/or incomplete electrical signals from the patient. Thus, it is important to detect a leads-off condition quickly so that someone, such as a medical technician, can correct the situation.

An example of an apparatus in which quick detection of a leads-off condition is paramount is a cardiac monitor that senses the ECG signal of a patient in order to determine the patient's cardiac activity and that senses the patient's transthoracic impedance in order to determine the patient's pulmonary activity. As is well known, a patient's cardiac activity and pulmonary activity must both be determined in order to decide upon an appropriate therapeutic measure, such as defibrillation. For example, if the normal sinus rhythm in a patient's ECG signal is absent, and the transthoracic impedance signal indicates an absence of breathing, a logical step would be to defibrillate the patient so as to stimulate the patient's heart. Contrariwise, if the normal sinus rhythm in the ECG signal is absent but the transthoracic impedance signal indicates the patient is still breathing, then the patient should not be defibrillated.

A method commonly employed by the prior art for detecting a leads-off condition is to sense lead impedance. The lead impedance actually comprises several impedances, such as an electrode impedance and a conductor impedance. Another impedance that makes up a significant part of the lead impedance is formed at an electrode-to-patient's skin connection. A leads-off condition that is produced by an electrode being detached from a patient produces a high electrode-to-skin connection impedance and therefore a high lead impedance.

One approach used in the prior art to sense lead impedance is to apply a small DC signal to the leads and to compare the resulting DC voltage to some threshold level. Typically, a DC voltage that equals or exceeds the threshold level is indicative of a leads-off condition. One such method is found in U.S. Pat. No. 4,577,639 (Simon et al.). A problem associated with this type of leads-off detection system is that the DC voltage that is used to sense the lead impedance may corrupt a physiological electrical signal (such as an ECG signal) present on that particular lead.

Another approach used by the prior art to detect a leads-off condition is to supply a high-frequency constant current signal to the leads. A return AC signal is demodulated and filtered to remove the physiological electrical signal (such as an ECG signal). The resulting signal is then compared to a threshold level to determine whether or not a leads-off condition exists. The demodulated signal may be further amplified and filtered to remove any DC components, thereby producing a signal that may be used to measure a patient's transthoracic impedance. Such an approach is found in U.S. Pat. No. 4,610,254 and its divisional U.S. Pat. No. 4,619,265 (Morgan et al.). One problem associated with this approach is that it is limited to systems using a single pair of electrodes.

Another problem associated with the prior art method of measuring a patient's transthoracic impedance is related to the size of the signal used and the size of the prior art apparatus. Typically, the prior art apparatus employ a transformer to produce a high frequency signal that is applied to the appropriate leads. Such a transformer is relatively large and inhibits miniaturization of the apparatus. This is an important consideration with portable apparatus, such as portable, multiple ECG lead apparatus. Also, the amplitude of the high frequency signals produced by the transformers in the prior art are typically too large for many electronic components used with the compact portable apparatus.

As can be readily appreciated from the foregoing discussion, there is a need for a method and apparatus that will provide both lead impedance and transthoracic impedance information for multiple-electrode systems (i.e., systems with two or more electrodes) without corrupting the physiological electrical signals present. Additionally, the apparatus should be small enough to be used with portable, multiple-electrode systems. The present invention is directed to a method and apparatus that provides these results.

SUMMARY OF THE INVENTION

In accordance with this invention, an apparatus for use with medical diagnostic and therapeutic apparatus employing electrodes attached to a patient's skin for sensing the integrity of lead connections and patient transthoracic impedance is provided. A lead and transthoracic impedance sensing apparatus comprises: a carrier signal source; a receiver; an amplifier; and a signal separator. The carrier signal source produces a first carrier signal and a second carrier signal that is out of phase with the first carrier signal, each having a lead impedance frequency component and an impedance respiration frequency component. The first carrier signal is applied to a first lead having a first lead impedance and the second carrier is applied to a plurality of second leads having a plurality of second lead impedances. A receiver receives a first lead voltage produced by the first carrier signal and the first lead impedance, and a plurality of second lead voltages produced by the second carrier signal and the plurality of second lead impedances. The amplifier amplifies the difference between combinations of the first lead voltage and each of the plurality of second lead voltages and produces a plurality of first stage output voltages and a plurality of second stage output voltages. The signal separator receives the plurality of first stage output voltages and produces a plurality of lead impedance-related voltages and one or more impedance respiration-related voltages.

In accordance with further aspects of this invention, the carrier signal source includes an impedance termination network through which the first and second carrier signals are applied to the first and second leads. The amplifier includes one or more fast DC restoration circuits that compensate for a DC offset in the second stage output voltages. The signal separator includes one or more fast DC restoration circuits, that compensate for a DC offset in the one or more impedance respiration-related voltages.

In accordance with still further aspects of this invention, a method for sensing the integrity of lead connections and patient transthoracic impedance is provided. The method comprises the steps of: producing first and second carrier signals, wherein the first carrier signal is out of phase with the second carrier signal; applying the first carrier signal to a first lead and the second carrier signal to a plurality of second leads; receiving a first lead voltage and a plurality of second lead voltages; amplifying the difference between the first lead voltage and each of the plurality of second lead voltages and producing a plurality of first stage output voltages and a plurality of second stage output voltages; and, producing a plurality of lead impedance-related voltages and one or more impedance respiration-related voltages from the first stage output voltages.

In accordance with yet further aspects of this invention, the step of amplifying includes the step of restoring the plurality of second stage output voltages to a nominal value by compensating for a DC offset. The step of producing one or more impedance respiration-related voltages includes the step of restoring the one or more impedance respiration-related voltages to a nominal value by compensating for a DC offset.

As will be readily appreciated from the foregoing summary, the invention provides a method and apparatus for sensing the integrity of lead connections and patient transthoracic impedance.

BRIEF DESCRIPTION OF THE DRAWINGS

The foregoing, and other features and advantages of this invention, will become more readily appreciated as the same becomes further understood by reference to the following detailed description when taken in conjunction with the accompanying drawings, wherein.

DETAILED DESCRIPTION OF THE PREFERRED EMBODIMENT

Figure 1:
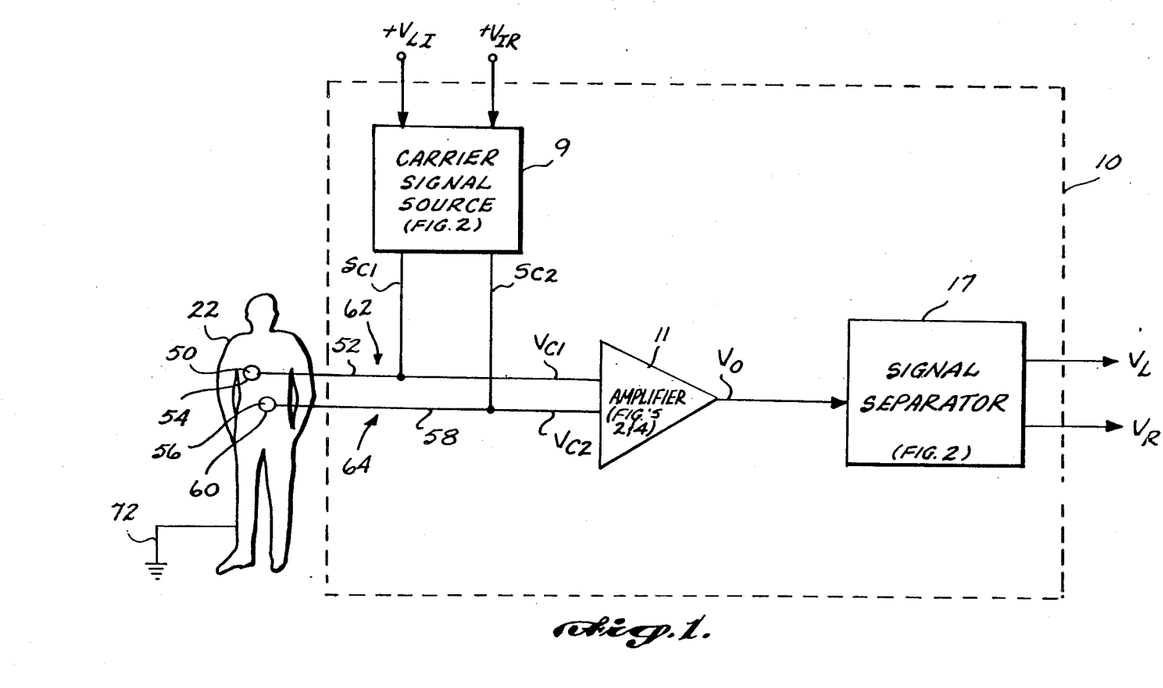
FIG. 1 is a simplified block diagram of an apparatus illustrating broad aspects of the present invention.

FIG. 1 illustrates, in simplified block diagram form, the broad aspects of the present invention. A lead and transthoracic impedance sensing apparatus 10 comprises: a carrier signal source 9; a two-input amplifier 11; and a signal separator 17. Electrical signals from a patient 22 are applied to the inputs of the amplifier 11. More specifically, a first electrode 50 is attached to the skin of the patient 22 and forms a first electrode-to-skin connection 54. A first conductor 52 is connected to one end to the first electrode 50 and at the other end to one input of the amplifier 11. The first electrode 50 and the first conductor 52 form a first lead 62. The first lead 62 has a lead impedance, designated $Z_{L1}$, which comprises several impedances, including an impedance of the electrode 50 and an impedance of the conductor 52. Another impedance that forms a significant part of $Z_{L1}$ is an impedance of the first electrode-to-skin connection 54, designated $Z_{54}$. A second electrode 56 is attached to the skin of the patient 22 and forms a second electrode-to-skin connection 60. A second conductor 58 is connected at one end to the second electrode 56 and at the other end to the other input of the amplifier 11. The second electrode 56 and the second electrode conductor 58 form a second lead 64. The second lead 64 has a lead impedance, designated $Z_{L2}$, which comprises several impedances, including an impedance of the electrode 56 and an impedance of the conductor 58. Another impedance that forms a significant part of $Z_{L2}$ is an impedance of the second electrode-to-skin connection 60, designated $Z_{60}$. The patient 22 is connected to a reference point 72, such as ground through a reference electrode, for example.

A lead impedance supply voltage, designated $V_{LI}$, and an impedance respiration supply voltage, designated $V_{IR}$, are applied to the inputs of the carrier signal source 9. The $V_{LI}$ and $V_{IR}$ voltages are AC signals whose frequencies are different from one another. A pair of carrier signals, designated $S_{C1}$ and $S_{C2}$, are produced by the carrier signal source 9. The $S_{C1}$ signal has the same frequency as the $S_{C2}$ signal, but is out of phase with $S_{C2}$. As will be better understood from the following discussion, both $S_{C1}$ and $S_{C2}$ are related to both $V_{LI}$ and $V_{IR}$. The $S_{C1}$ signal is applied to the first conductor 52 and the $S_{C2}$ signal is applied to the second conductor 58. As will be better understood from the following discussion, the amplifier 11 acts as a receiver to receive voltages produced, in part, by the $S_{C1}$ and $S_{C2}$ signals. A first input voltage, designated $V_{C1}$, is produced by the $S_{C1}$ signal and $Z_{L1}$ and is applied to one input of the amplifier 11 via the first conductor 52. A second input voltage, designated $V_{C2}$, is produced by the $S_{C2}$ signal and $Z_{L2}$ and is applied to the other input of the amplifier 11 via the second conductor 58. Since the $S_{C1}$ and $S_{C2}$ signals are out of phase with each other, the $V_{C1}$ and $V_{C2}$ voltages are also out of phase with each other. As will be better understood from the following discussion, the amplifier 11 amplifies the difference between the $V_{C1}$ and $V_{C2}$ voltages and produces an output voltage, designated $V_O$.

The $S_{C1}$ and $S_{C2}$ signals each comprise two frequency components: a lead impedance frequency component, designated $S_{LI}$, produced by $V_{LI}$, and an impedance respiration frequency component, designated $S_{IR}$, produced by $V_{IR}$. The frequencies of the $S_{LI}$ and $S_{IR}$ components are the same as the frequencies of the $V_{LI}$ and $V_{IR}$ voltages, respectively. As a result, both of the $V_{C1}$ and $V_{C2}$ voltages contain components produced by $S_{LI}$ and $S_{IR}$. More specifically, $V_{C1}$ comprises a lead impedance component voltage, designated $V_{1LI}$, produced by the $S_{LI}$ component of the $S_{C1}$ signal and $Z_{L1}$, and an impedance respiration component voltage, designated $V_{1IR}$, produced by the $S_{IR}$ component of the $S_{C1}$ signal and $Z_{L1}$. Likewise, $V_{C2}$ comprises a lead impedance component voltage, designated $V_{2LI}$, produced by the $S_{LI}$ component of the $S_{C2}$ signal and $Z_{L2}$, and an impedance respiration component voltage, designated $V_{2IR}$, produced by the $S_{IR}$ component of the $S_{C2}$ signal and $Z_{L2}$. Because, as noted above, the $S_{C1}$ and $S_{C2}$ signals are out of phase with each other, $V_{1LI}$ is out of phase with $V_{2LI}$ and $V_{1IR}$ is out of phase with $V_{2IR}$. As a result, the $V_O$ voltage comprises two components, namely a lead impedance-related voltage, designated $V_L$, and an impedance respiration-related voltage, designated $V_R$. The $V_{OLI}$ and $V_{OIR}$ voltages are produced by the amplifier 11 and are the amplified differences between $V_{1VI}$ and $V_{2LI}$, and $V_{1IR}$ and $V_{2IR}$, respectively.

The signal separator 17 is controlled in such a manner that the $V_L$ and $V_R$ voltages are extracted from $V_O$. As will also be better understood from the following discussion, the $V_L$ voltage is proportional to a combination of the lead impedances, $Z_{L1}$ and $Z_{L2}$, which include the electrode-to-skin connection impedances, $Z_{54}$ and $Z_{60}$, and the $V_R$ voltage is proportional to a patient's transthoracic impedance, designated $Z_T$, which is discussed below. The frequency of the $S_{LI}$ signal is selected so that the resulting $V_L$ voltage varies linearly with $Z_{L1}$ and $Z_{L2}$ for a particular range of $Z_{54}$ and $Z_{60}$ values. Likewise, the $S_{IR}$ signal frequency is selected so that the resulting $V_R$ voltage varies linearly with small changes in $Z_T$ within the same range of values for $Z_{54}$ and $Z_{60}$. Thus, the lead and transthoracic impedance sensing apparatus 10 produces voltages (i.e., $V_L$ and $V_R$) that are proportional to the lead impedances (i.e., $Z_{L1}$ and $Z_{L2}$) and the patient's transthoracic impedance (i.e., $Z_T$), respectively. Downstream devices, which do not form a part of this invention, may be used to analyze $V_L$ and $V_R$ to determine whether a leads-off condition exists and the patient's pulmonary activity.

Figure 2:
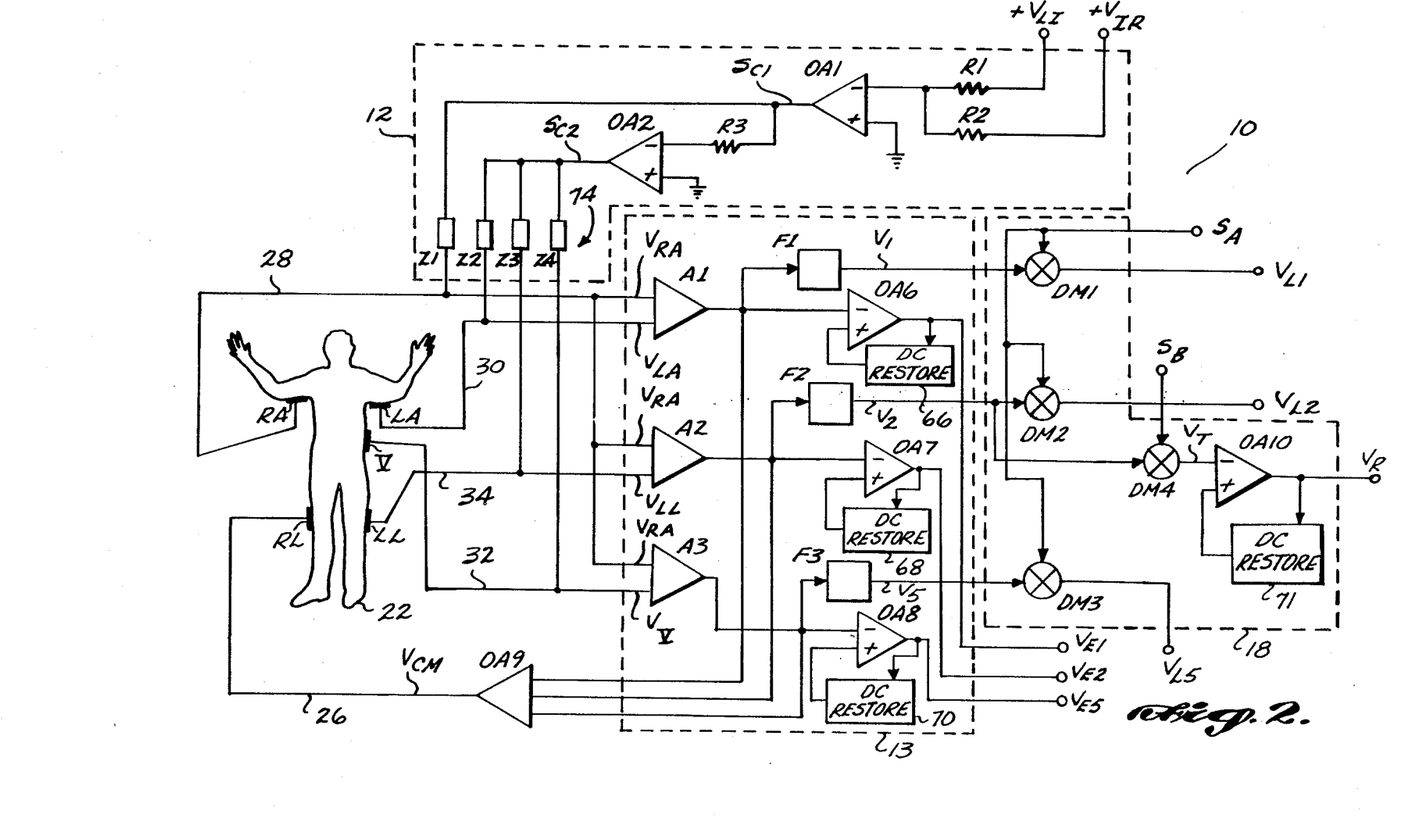
FIG. 2 is a schematic diagram of a preferred embodiment of the apparatus illustrated in FIG. 1.

FIG. 2 is a schematic diagram of a preferred embodiment of the lead and transthoracic impedance sensing apparatus 10 illustrated in FIG. 1 and discussed above. The apparatus 10 illustrated in FIG. 2 comprises: a carrier circuit 12, an ECG preamplifier 13; and, a demodulator circuit 18. In accordance with the preferred embodiment of the invention, the carrier circuit 12, the ECG preamplifier 13 and the demodulator circuit 18 perform the respective functions of the carrier signal source 9, the amplifier 11 and the signal separator 17 illustrated in FIG. 1. In one particular application of the invention, the patient 22 is connected to a cardiac monitor employing four active ECG electrodes, designated RA, LA, LL and V, and one inactive, or reference, electrode, designated RL. As is well known in the medical electrode art, the RA electrode is attached to the patient's right arm, the LA electrode is attached to the patient's left arm, the LL electrode is attached to the patient's left leg and the RL electrode is attached to the patient's right leg. The V electrode is a "free" electrode attached to the patient 22 and is typically moved about various locations in the area of the patient's lower heart region. As is also well known in the art, a cardiac monitor employing multiple active ECG electrodes (such as the RA, LA, LL, and V electrodes) operates in such a manner that different aspects of the patient's cardiac activity can be sensed by different combinations of the active electrodes. For example, in a Leads I mode, the cardiac monitor senses patient ECG signals with the RA and LA electrodes, during a Leads II mode, the RA and LL electrodes are used and during a Leads V mode, the RA and V electrodes supply the patient ECG signals to the monitor. Obviously, numerous other electrode combinations may be used to provide medical personnel with information on the patient's cardiac activity. It is to be understood that applications of the present invention are not limited to the electrode combinations discussed herein.

As will be better understood from the following discussion, the RA, LA, LL and V electrodes are connected to the inputs of the ECG preamplifier 13. More specifically, the RA electrode is connected to one end of an RA conductor 28. The other end of the RA conductor 28 is connected to inputs of three first stage amplifiers, designated A1, A2, and A3, located in the ECG preamplifier 13, which is discussed below. The LA electrode is connected to another input of A1 via an LA conductor 30. The LL electrode is connected to another input of A2 via an LL conductor 34. The V electrode is connected to another input of A3 via a V conductor 32. The RL electrode is connected to the output of a common mode drive amplifier, designated OA9, via an RL conductor 26. OA9 has three inputs which are connected to the outputs of A1, A2, and A3. The RL electrode, the RL conductor 26 and OA9 perform the function of the reference point 72 illustrated in FIG. 1 and discussed above. The patient 22, the RA, LA, LL, RL and V electrodes, the electrode conductors 26, 28, 30, 32 and 34 and OA9 are illustrated in FIG. 2 and discussed herein for purposes of completeness and clarity in understanding the present invention and do not form a part of this invention.

A lead, designated RA lead, comprises the RA electrode and the RA conductor 28. The RA lead has a lead impedance, designated $Z_{RA}$, which comprises several impedances including impedances of: the RA conductor 28; the RA electrode; an RA electrode-to-skin connection; and, an internal impedance of the patient 22. Likewise, an LA lead comprises the LA electrode and the LA conductor 30. The LA lead has a lead impedance, designated $Z_{LA}$, that includes impedances of: the LA conductor 30; the LA electrode; an LA electrode-to-skin connection; and, an internal impedance of the patient 22. An LL lead comprises the LL electrode and the LL conductor 34. The LL lead has a lead impedance, designated $Z_{LL}$, that includes impedances of: the LL conductor 34; the LL electrode; an LL electrode-to-skin connection; and, an internal impedance of the patient 22. Lastly, a V lead comprises the V electrode and the V conductor 32. The V lead has a lead impedance, designated $Z_V$, that comprises impedances of: the V conductor 32, the V electrode, a V electrode-to-skin connection; and, an internal impedance of the patient 22. The RL electrode and the RL conductor 26 also form a lead, designated RL lead, which has a lead impedance, designated $Z_{RL}$. Because the RL lead is not connected to an active electrode (i.e., RA, LA, LL, or V) it is not discussed further.

During normal operating conditions, i.e., when the electrodes are attached to the patient 22 and the conductors are connected between the appropriate electrodes and the cardiac monitor, the electrode-to-skin connection impedances are typically the most significant impedance components of $Z_{RA}$, $Z_{LA}$, $Z_{LL}$, and $Z_V$. For example, the electrode-to-skin impedances may be several hundred thousand ohms whereas: the patient's internal impedance is typically only a few hundred ohms; the electrode impedances are typically only a few hundred ohms; and, the electrode conductor impedance is typically about a thousand ohms. Thus, as will be better understood from the following discussion, the lead and transthoracic impedance sensing apparatus 10 continuously senses the impedances of the electrode-to-skin connections which, as noted above, form, in part, the lead impedances, $Z_{RA}$, $Z_{LA}$, $Z_{LL}$, and $Z_V$.

As will also be better understood from the following discussion, the apparatus 10 continuously senses the impedance respiration of the patient 22 by sensing the patient's transthoracic impedance, $Z_T$, noted above, $Z_T1$ is an impedance associated with the chest cavity of the patient 22 and forms a part of the patient's internal impedance discussed above. $Z_T$ varies with the pulmonary activity of the patient 22. These variations in $Z_T$ are sensed by the apparatus 10. In one particular embodiment, $Z_T$ is sensed with the RA and LL leads.

Turning to the lead and transthoracic impedance sensing apparatus 10, a more detailed description of the various portions of the apparatus 10 noted above is presented next. The carrier circuit 12 produces the $S_{C1}$ and $S_{C2}$ signals which, as discussed above, have the same frequencies as each other but are not out of phase with each other. The carrier circuit 12 illustrated in FIG. 2 comprises: two operational amplifiers, designated OA1 and OA2; three resistors, designated R1, R2 and R3; and, a terminating impedance network 74. The terminating impedance network 74 comprises four terminating impedances, designated Z1, Z2, Z3 and Z4. The lead impedance and impedance respiration supply voltages, $V_{LI}$ and $V_{IR}$, noted above, are applied to the inverting input of OA1 through R1 and R2, respectively. The noninverting input of OA1 is grounded. The output of OA1 is connected to one end of Z1 and to the inverting input of OA2 through R3. The noninverting input of OA2 is grounded. The output of OA2 is connected to one end of Z2, Z3 and Z4. The other end of Z1 is connected to the RA conductor 28. The other end of Z2 is connected to the LA conductor 30, the other end of Z3 is connected to the LL conductor 34, and the other end of Z4 is connected to the V conductor 32. The $S_{C1}$ and $S_{C2}$ carrier signals are formed at the outputs of OA1 and OA2, respectively. The terminating impedances, Z1, Z2, Z3 and Z4 permit the $S_{C1}$ and $S_{C2}$ carrier signals to be applied to the conductors 28, 30, 32, and 34 without the use of a transformer, such as is used in the prior art. The terminating impedance network 74 (i.e., Z1, Z2, Z3, and Z4) will be discussed in greater detail below.

The $V_{LI}$ and $V_{IR}$ voltages are weighted by R1 and R2 are summed at the input of OA1. Preferably, R1 is substantially larger than R2 and, for example, R1 may be ten times the size of R2 (i.e., R1=10R2). As discussed above, the $S_{C1}$ signal formed at the output of OA1 includes the frequency components, $S_{LI}$ and $S_{IR}$, which are derived from, and have the same frequencies as, the $V_{LI}$ and $V_{IR}$ voltages, respectively. The ratio of the amplitudes of the $S_{LI}$ and $S_{IR}$ components is inversely proportional to the ratio of R1 and R2 (i.e., in the above example, $S_{IR}=10S_{LI}$). OA2 inverts the $S_{C1}$ signal to produce the $S_{C2}$ signal. Thus, in accordance with the preferred embodiment of the invention, $S_{C2}$ has the opposite polarity of $S_{C1}$. The $S_{C1}$ signal is applied to the RA conductor 28 and the $S_{C2}$ signal is applied to the LA conductor 30, the V conductor 32 and the LL conductor 34.

An RA lead voltage, designated $V_{RA}$, is produced by $S_{C1}$ and $Z_{RA}$ and is applied to one input of A1, A2 and A3 via conductor 28. An LA lead voltage, designated $V_{LA}$ is produced by $S_{C2}$ and $Z_{LA}$ and is applied to the other input of A1. An LL lead voltage, designated $V_{LL}$, is produced by $S_{C2}$ and $Z_{LL}$ and is applied to the other input of A2. A V lead voltage, designated $V_V$, is produced by $S_{C2}$ and $Z_V$ and is applied to the other input of A3. Because $S_{C1}$ is out of phase with $S_{C2}$, the $V_{RA}$ voltage is out of phase with the $V_{LA}$, $V_{LL}$ and $V_V$ voltages. As will be better understood from the following discussion, A1, A2 and A3 amplify the difference between the out-of-phase lead voltages applied to their respective inputs. In addition to the amplified difference between the lead voltages, the outputs of A1, A2 and A3 also contain other electrical signals, such as patient ECG signals, for example. As will be better understood from the following discussion, the other electrical signals (i.e., ECG signals) are filtered out of the amplifier outputs by high pass filters that form a part of the present invention.

The ECG preamplifier 13 receives the $V_{RA}$, $V_{LA}$, $V_{LL}$ and $V_V$ voltages and, as noted above, amplifes the difference between these voltages. The preamplifier illustrated in FIG. 2 comprises: the three first stage amplifiers, A1, A2 and A3, discussed above; three high pass filters, designated F1, F2, and F3; three second stage operational amplifiers, designated OA6, OA7 and OA8; and, three DC restoration circuits 66, 68, and 70. The demodulator circuit 18 comprises: three lead impedance demodulators, designated DM1, DM2 and DM3; one impedance respiration demodulator, designated DM4; one operational amplifier, designated OA10; and, one DC restoration circuit 71. Each of DM1, DM2, DM3 and DM4 has one analog signal input, a clock input, and one output. The DC restoration circuits 66, 68, 70 and 71 illustrated in block diagram form in FIG. 2, are further illustrated in FIG. 5 and discussed more fully below.

The output of A1 is connected to the inverting input of OA6 and to the input of F1. The output of F1 is connected to the analog input of DM1. The output of OA6 is connected to the input of the DC restoration circuit 66. The output of the DC restoration circuit 66 is connected to the noninverting input of OA6. The output of A2 is connected to the inverting input of OA7 and to the input of F2. The output of F2 is connected to the analog units of DM2 and DM4. The output of DM4 is connected to the inverting input of OA10. The output of OA10 is connected to the input of the DC restoration circuit 71. The output of the DC restoration circuit 71 is connected to the noninverting input of OA10. The output of OA7 is connected to the input of the DC restoration circuit 68. The output of the DC restoration circuit 68 is connected to the noninverting unit of OA7. The output of A3 is connected to the inverting input of OA8 and to the input of F3. The output of F3 is connected to the analog input of DM3. The output of OA8 is connected to the input of the DC restoration circuit 70. The output of the DC restoration circuit 70 is connected to the noninverting input of OA8. As discussed above, the outputs of A1, A2 and A3 are also connected to the inputs of OA9.

As noted above, the differences between the lead voltages are amplified by A1, A2 and A3. More specifically: A1 amplifies the difference between $V_{RA}$ and $V_{LA}$ and applies an output voltage to F1 and OA6; A2 amplifies the difference between $V_{RA}$ and $V_{LL}$ and applies an output voltage to F2 and OA7; and, A3 amplifies the difference between $V_{RA}$ and $V_V$ and applies an output voltage to F3 and OA8. As noted above, the high pass filters (i.e., F1, F2 and F3) remove low-frequency electrical signals, such as the patient ECG signals, from the output voltages of A1, A2, and A3. First-stage output voltages, designated $V_1$, $V_2$ and $V_5$, are formed at the outputs of F1, F2, and F3, respectively. As will be better understood from the following discussion, the $V_1$, $V_2$ and $V_5$ voltages are comprised of voltage components formed by the $S_{C1}$ and $S_{C2}$ carrier signals and, as a result, the voltage components of $V_1$, $V_2$ and $V_5$ are lead impedance and impedance respiration-related voltage components. Second-stage output voltages, designated $V_{E1}$, $V_{E2}$ and $V_{E5}$, are formed at the outputs of OA6, OA7 and OA8, respectively. In the particular embodiment of the invention set forth in FIG. 2 and discussed above, the $V_{E1}$, $V_{E2}$ and $V_{E5}$ voltages include the patient ECG signals.

A first control signal, designated $S_A$, is applied to the clock inputs of DM1, DM2 and DM3. The $S_A$ signal has a frequency that is equal to the frequency of the $S_{LI}$ component discussed above. A second control signal, designated $S_B$, is applied to the clock input of DM4. The $S_B$ signal has a frequency that is equal to the frequency of the $S_{IR}$ component also discussed above. The $S_A$ and $S_B$ signals are produced in a conventional manner, and may, for example, be a series of pulses, the frequency of which are the same as the frequencies of $S_{LI}$ and $S_{IR}$, respectively. Accordingly, DM1, DM2 and DM3 demodulate the $V_1$, $V_2$ and $V_5$ voltages at the $S_{LI}$ frequency so as to produce lead impedance-related voltages, designated $V_{L1}$, $V_{L2}$ and $V_{L5}$.

As will be better understood from the following discussion, $V_{L1}$, $V_{L2}$ and $V_{L5}$ are proportional to the impedances formed by various combinations of $Z_{RA}$, $Z_{LA}$, $Z_{LL}$ or $Z_V$. More specifically, during ECG Leads I sensing, $V_{L1}$ is proportional to a series combination of $Z_{RA}$ and $Z_{LA}$. Likewise, during ECG Leads II sensing, $V_{L2}$ is proportional to a series combination of $Z_{RA}$ and $Z_{LL}$, and during ECG Leads V sensing, $V_{L5}$ is proportional to a series combination of $Z_{RA}$ and $Z_V$. The $V_{L1}$, $V_{L2}$ and $V_{L5}$ voltages may be processed by any number of downstream devices, such as comparators, for example, so as to determine whether a leads-off condition exists. These downstream devices are well known in the art and do not form a part of this invention.

DM4 demodulates the $V_2$ voltage at the $S_{IR}$ frequency so as to produce a transthoracic impedance-related voltage, designated $V_T$, from which is derived an impedance respiration-related voltage, designated $V_R$. As will become better understood from the following discussion, the $V_T$ voltage is proportional to the patient's transthoracic impedance, $Z_T$. In accordance with the preferred embodiment of the invention, $V_T$ is produced by the Leads II combination of electrodes (i.e., the RA and LL electrodes). The $V_T$ voltage is further amplified by OA10 and the DC restoration circuit 71 to produce the $V_R$ voltage, which corresponds to small changes in $V_T$. The $V_R$ voltage can be measured by a downstream voltage measurement device or processed by some other downstream device, such as a comparator, for example. Such downstream devices are well known and do not form a part of this invention.

Turning next to the impedance respiration network 74, values for Z1, Z2, Z3, and Z4 are selected so that the lead and transthoracic impedance sensing apparatus 10 will produce meaningful lead impedance information (i.e., $V_{L1}$, $V_{L2}$, and $V_{L5}$) and impedance respiration information (i.e., $V_R$) for a particular range of electrode-to-skin impedances. For example, as is well known in the medical electrode art, a range of 50 kΩ to 620 kΩ is an acceptable range of ECG electrode-to-skin impedances for nominal ECG electrode operation. The values of $Z_1$, $Z_2$, $Z_3$ and $Z_4$ are selected so that for a particular frequency (such as the $S_{LI}$ frequency), the lead impedance voltages ($V_{L1}$, $V_{L2}$ and $V_{L5}$) will vary linearly with changes in $Z_{RA}$, $Z_{LA}$, $Z_{LL}$ and $Z_V$ within a given range of electrode-to-skin impedances (i.e., 50 kΩ–620 kΩ). The $Z_1$, $Z_2$, $Z_3$ and $Z_4$ values are also selected so that for another frequency (such as the $S_{IR}$ frequency), the impedance respiration voltage ($V_R$) will be sensitive to small changes in the patient's transthoracic impedance, $Z_T$, within the same range of electrode-to-skin impedances. In one particular embodiment of the invention, an $S_{LI}$ frequency of 1024 Hz (hereinafter referred to as 1 kHz) and an $S_{IR}$ frequency of 18.432 kHz (hereinafter referred to as 18 kHz) were selected. Obviously, other frequencies can be selected, and it is to be understood that the present invention is not limited to the $S_{LI}$ and $S_{IR}$ frequencies discussed herein.

Figure 3:
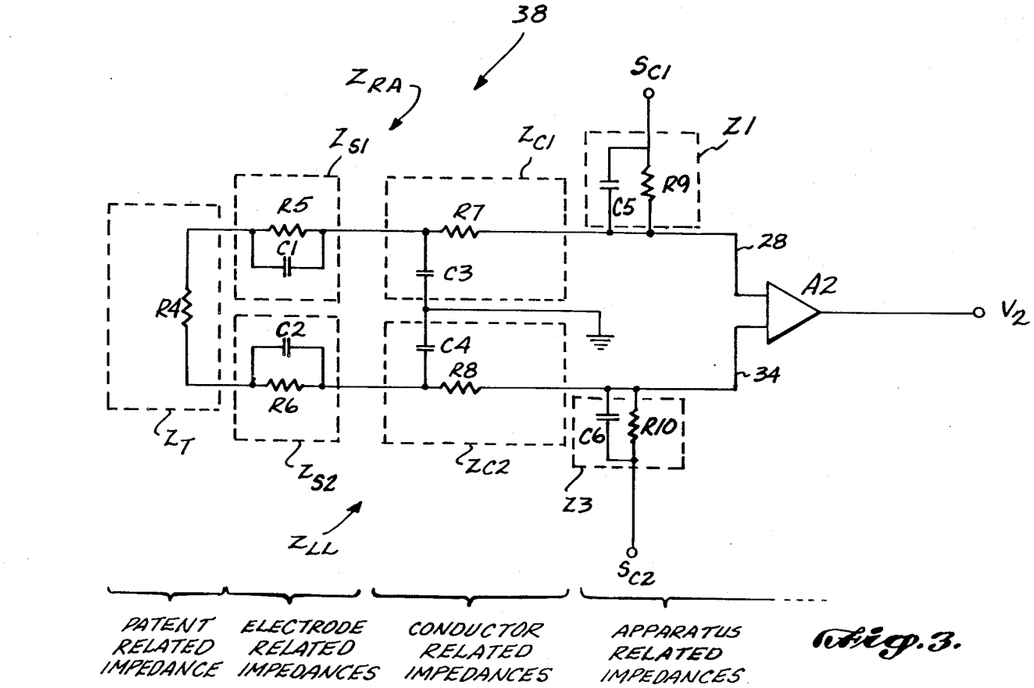
FIG. 3 is a more detailed schematic diagram of lead and terminating impedances for a portion of the apparatus illustrated in FIG. 2.

FIG. 3 is a schematic diagram of a Leads II electrode combination 38 illustrating, in more detail, the terminating impedances, Z1 and Z3, and portions of the RA and LL lead impedances (i.e., $Z_{RA}$ and $Z_{LL}$). The exemplary Leads II electrode combination 38 comprises: the two terminating impedances, Z1 and Z3, of the lead and transthoracic impedance sensing apparatus 10, discussed above; two capable impedances, designated $Z_{C1}$ and $Z_{C2}$, associated with the RA and LL conductors 28 and 34, in which, in accordance with the preferred embodiment of the invention, may be standard ECG patient cables; two electrode-to-skin impedances associated with the RA and LL electrodes, designated $Z_{S1}$ and $Z_{S2}$; and, the patient's transthoracic impedance, $Z_T$. In addition to depicting the aforementioned impedances in the schematic diagram in FIG. 3, FIG. 3 further illustrates the physical locations of the various impedances. This is illustrated by the brackets in FIG. 3. In accordance with the particular embodiment illustrated in FIG. 3, the RA lead impedance, $Z_{RA}$, discussed above, comprises: $Z_{C1}$; $Z_{S1}$; and, $Z_T$, and the LL lead impedance, $Z_{LL}$, also discussed above, comprises: $Z_{C2}$; $Z_{S2}$; and, $Z_T$. The Z1 impedance comprises a parallel combination of one capacitor, designated C5, and one resistor, designated R9. Likewise, the Z3 impedance comprises a parallel combination of one capacitor, designated C6, and one resistor, designated R10. The $Z_{C1}$ cable impedance comprises one resistor, designated R7, and one capacitor, designated C3. The $Z_{C2}$ cable impedance comprises one resistor, designated R8, and one capacitor, designated C4. R7 and R8 represent current limiting resistors typically found in standard ECG patient cables, such as the RA and LL conductors. C3 and C4 represent typical lead-to-shield capacitances of standard ECG patient cables, such as the RA and LL conductors. The $Z_{S1}$ electrode-to-skin impedance comprises a parallel combination of one resistor, designated R5, and one capacitor, designated C1. Likewise, the $Z_{S2}$ electrode-to-skin impedance comprises a parallel combination of one resistor, designated R6, and one capacitor, designated C2. The $Z_T$ impedance comprises one resistor, designated R4.

As illustrated in FIG. 3, one end of the parallel combination of C5 and R9 (i.e., Z1) is connected to one input of A2 (FIG. 2) and to one end of R7. The $S_{C1}$ carrier signal is applied to the other end of the parallel combination of C5 and R9. One end of the parallel combination of C6 and R10 (i.e., Z3) is connected to the other input of A2 and to one end of R8. The $S_{C2}$ carrier signal is applied to the other end of the parallel combination of C6 and R10. The other end of R7 is connected to ground through C3 and to one end of the parallel combination of R5 and C1. The other end of R8 is connected to ground through C4 and to one end of the parallel combination of R6 and C2. The other end of the parallel combination of R6 and C2 is connected to the other end of the parallel combination of R5 and C1 through R4.

Typical values for the RA and LL lead impedances illustrated in FIG. 3 can be readily determined by conventional methods and are well known in the art. For example, typical values for $Z_{C1}$ and $Z_{C2}$ may be: 1 k$\Omega$ for R7 and R8; and, 500 pf for C3 and C4. Likewise, typical values for $Z_{S1}$ and $Z_{S2}$ may be: 100 k$\Omega$ for R5 and R6; and, 4.7 nf for C1 and C2. A typical value for $Z_T$ may be 100$\Omega$ (i.e., R4=100$\Omega$). In the particular embodiment discussed above (i.e., $S_{LI}$=1 kHz and $S_{IR}$=18 kHz), using the typical impedance values discussed above, appropriate values for $Z_1$ and $Z_3$ might be: 5 M$\Omega$ for R9 and R10; and, 240 pf for C5 and C6. Preferably, under normal conditions, the other leads (i.e., LA and V) have the same impedance values, with the possible exception of $Z_T$. The value of $Z_T$ may vary slightly depending upon electrode placement on the patient. Accordingly, the terminating impedances are preferably the same for the RA, LA, LL and V electrodes (i.e., Z1=Z2=Z3=Z4).

Figure 4A:
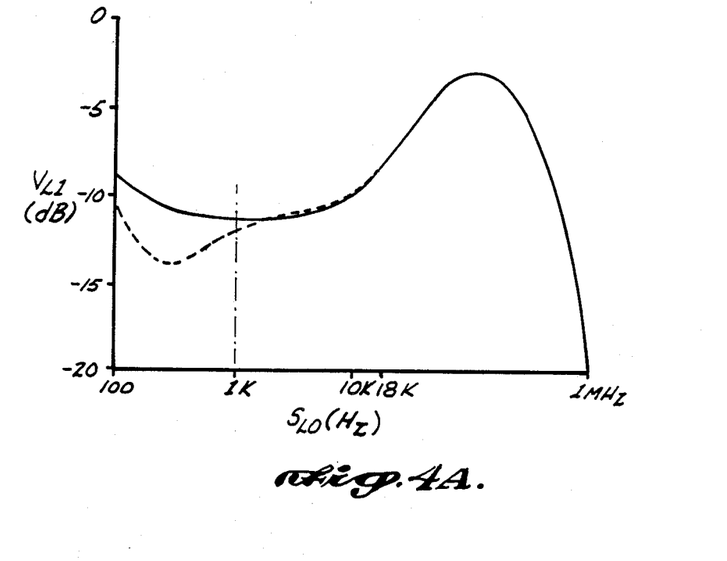
FIGS. 4 and 4B are graphs illustrating exemplary lead impedance and transthoracic impedance-related voltages produced by the apparatus in FIG. 2; and, FIG. 5 is a simplified schematic diagram of a DC restoration circuit suitable for use in the apparatus illustrated in FIG. 2.
Figure 4B:
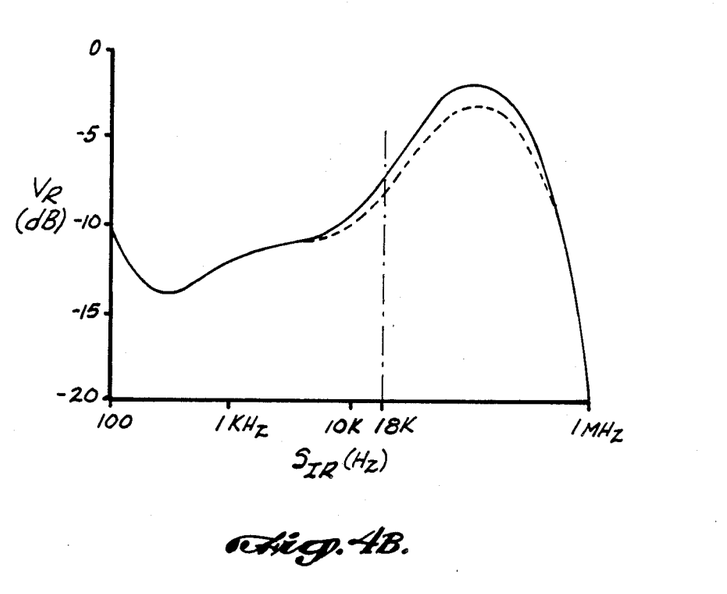

As will be better understood from the following discussion, and with reference to FIGS. 4A and 4B, the values for Z1, Z2, Z3 and Z4 and the frequencies of $S_{LI}$ and $S_{IR}$ set forth in the above examples, result in the lead impedance-related voltages, $V_{L1}$, $V_{L2}$ and $V_{L5}$, and the impedance respiration-related voltage, $V_R$, that can be analyzed by downstream components that will detect a leads-off condition and determine the patient's pulmonary activity. It is to be understood that FIG. 3 is merely exemplary in nature and that the apparatus 10 of the present invention is not limited to the impedances illustrated in FIG. 3 and discussed above. Likewise, it is to be understood that FIG. 3 is also representative of the Leads I and Leads V electrode combinations (i.e., RA electrode-LA electrode and RA electrode-V electrode, respectively). However, in accordance with the preferred embodiment of the invention, $Z_T$ is not measured in the Leads I and Leads V arrangements.

FIGS. 4A and 4B illustrate representative lead impedance-related voltages, $V_{L1}$, $V_{L2}$ and $V_{L5}$, and an impedance respiration-related voltage, $V_R$, produced by the lead and transthoracic impedance sensing apparatus 10 in the particular embodiment of the invention illustrated in FIGS. 2 and 3 and discussed above. FIG. 4A is a graph illustrating how the amplitude of a lead impedance-related voltage (such as $V_{L1}$, for example), varies with changes in the resistance (i.e., R5 and R6 in FIG. 3) of the electrode-to-skin impedances, $Z_{S1}$ and $Z_{S2}$ (FIG. 3). The X-axis represents a range of $S_{LI}$ frequencies bounded on the low-frequency end by 100 Hz and on the high-frequency end by 1 MHz. The Y-axis represents the amplitude of $V_{L1}$ in decibels (dB). A lower (dashed) curve represents $V_{L1}$ as a function of $S_{LI}$ frequency for a low R5 or R6 value (such as 50 k$\Omega$, for example). The upper (solid) curve represents $V_{L1}$ as a function of $S_{LI}$ frequency for a high R5 or R6 value (such as 620 k$\Omega$, for example). As can be seen from FIG. 4A, in the lower $S_{LI}$ frequency range, $V_{L1}$ has different values for different values of R5 and R6, whereas at the higher end of the $S_{LI}$ frequency range, $V_{L1}$ varies in the same manner for different values of R5 and R6. Thus, by selecting an appropriate $S_{LO}$ frequency, such as the 1 kHz frequency in the above example (indicated by the vertical dashed line), the $V_{L1}$ voltage varies with changes in $Z_{S1}$ and $Z_{S2}$ (i.e., R5 and R6). As discussed above, the resulting lead impedance voltage ($V_{L1}$) can be measured by devices not forming a part of this invention to determine, for example, whether a leads-off condition exists. Obviously, the $V_{L2}$ and $V_{L5}$ voltages react in a manner similar to that discussed above for the $V_{L1}$ voltage.

Turning next to the impedance respiration portion of the present invention, FIG. 4B is a graph illustrating how the amplitude of the impedance respiration-related voltage, $V_R$, varies with changes in the resistance (i.e., R4 in FIG. 3) of the patient's transthoracic impedance, $Z_T$. The X-axis represents a range of $S_{IR}$ frequencies between 100 Hz and 1 MHz. The Y-axis represents the amplitude of $V_R$ in dB. A lower (dashed) curve represents $V_R$ as a function of $S_{IR}$ frequency for a low R4 value (such as 100$\Omega$, for example). An upper (solid) curve represents $V_R$ as a function of $S_{IR}$ frequency for a high R4 value (such as 500$\Omega$, for example). As can be seen from FIG. 4B, in the higher end of the $S_{IR}$ frequency range, $V_R$ has different values for different values of R4, whereas, in the lower end of the $S_{IR}$ frequency range, $V_R$ varies in the same manner for different values of R4. Thus, by selecting an appropriate $S_{IR}$ frequency, such as the 18 kHz frequency in the above example (indicated by the vertical dashed line), the $V_R$ voltage varies with changes in the patient's transthoracic impedance, $Z_T$ (i.e., R4). As discussed above, the resulting $V_R$ volage can be measured by devices not forming a part of this invention the pulmonary activity of the patient 22.

Figure 5:
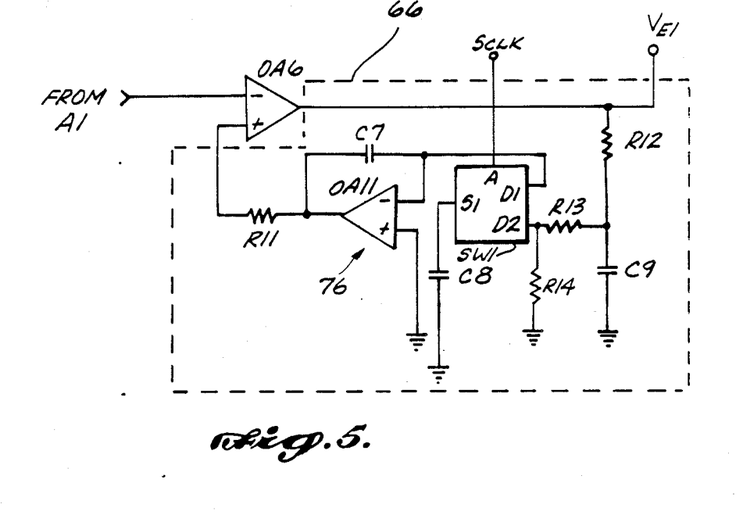

FIG. 5 is a schematic diagram illustrating the fast DC restoration feature of the ECG preamplifier 13 and the demodulator circuit 18 noted above and illustrated in FIG. 2. As will be better understood from the following discussion, DC restoration is necessary to correct a change, or DC offset, introduced into the output of the ECG preamplifier 13 (i.e., $V_{E1}$, $V_{E2}$ and $V_{E5}$) or into the impedance respiration-related voltage, $V_R$. As is well known in the art, such an offset may be caused by an event, such as a defibrillation pulse or the changing or moving of an ECG electrode on a patient, for example. This DC offset must be corrected so that the output of the preamplifier 13 and the $V_R$ voltage are restored to nominal values; otherwise an erroneous ECG signal and/or $V_R$ voltage may be produced. Thus, when an event causes such a DC offset it is important to restore the $V_{E1}$, $V_{E2}$, $V_{E5}$ and $V_R$ voltages to nominal values as quickly as possible. As will be understood from the following discussion, the fast DC restoration feature of the present invention uses a switched capacitor integrator that compensates for a DC offset more rapidly than prior art methods.

The circuit illustrated in FIG. 5 is duplicated for each of the three second stage operational amplifiers in the ECG preamplifier 13, i.e., OA6, OA7 and OA8, and the impedance respiration operational amplifier in the demodulator circuit 18, i.e., OA10, illustrated in FIG. 2. For ease of discussion, FIG. 5 illustrates the DC restoration circuit 66 associated with OA6. The DC restoration circuit 66 comprises: one operational amplifier, designated OA11; one switched-capacitor integrator 76; four resistors, designated R11, R12, R13 and R14; and two capacitors, designated C8 and C9. The switched-capacitor integrator 76 comprises: one solid-state switch, designated SW1; one operational amplifier, designated OA11; and, one feedback capacitor, designated C7. SW1 comprises: one signal input, S1; one control input, A; and, two signal outputs, D1 and D2. The output of OA6 is connected to one end of R12. The other end of R12 is connected to ground through C9 and to one end of R13. The other end of R13 is connected to the D2 output of SW1 and to ground through R14. The D1 output of SW1 is connected to the inverting input of OA11 and to the output of OA11 through C7. The S1 input of SW1 is connected to ground through C8. A DC restoration clock signal, designated $S_{CLK}$, is applied to the A input of SW1. The noninverting input of OA11 is connected to ground. The output of OA11 is connected to the noninverting input of OA6 through R11. As noted above and illustrated in FIG. 2, the inverting input of OA6 is connected to the output of A1 in the preamplifier 13 (connections not shown in FIG. 5.) The $V_{E1}$ voltage is formed at the output of OA6 and, as noted above, contains the patient ECG signals.

The output of OA6 is a nominal value when there is no DC offset in the $V_{E1}$ voltage. As will be better understood from the following discussion, the circuit in FIG. 5 restores the output of OA6 to a nominal value when $S_{CLK}$ pulses are applied to SW1. The detection of a DC offset in the $V_{E1}$ voltage can be performed in a conventional manner that is well known in the art and, as such, does not form a part of this invention. Likewise, the $S_{CLK}$ pulses are generated in a conventional manner which also does not form a part of the present invention. Furthermore, the $S_{CLK}$ signal is produced so that the $S_{CLK}$ pulses occur at a first, or low, frequency when a low DC offset is detected, and at a second, or high, frequency when an excessive DC offset is detected. Such an excessive DC offset might be caused by a defibrillation pulse, for example. The determination of whether a detected DC offset is a low or excessive level is made in a conventional manner, such as with a comparator, for example, and does not form part of this invention.

In the absence of an $S_{CLK}$ pulse, the S1 input is connected to the D2 output of SW1 and C8 is charged by OA6 to a voltage equal to the voltage drop across R14. When an $S_{CLK}$ pulse is applied to the A input of SW1, SW1 connects the S1 input to the D1 output. This causes C8 to charge C7. The output of OA11 is applied to OA6 and $V_{E1}$ is returned to a nominal level.

As will be better understood from the following discussion, the switched-capacitor integrator 76 allows the DC restoration circuit 66, illustrated in FIG. 5, to compensate for a DC offset in the $V_{E1}$ voltage and restore $V_{E1}$ to a nominal value much faster than conventional DC restoration methods found in the prior art. Conventional methods typically use an RC integrator, in which input resistor(s) are relatively small (such as 5 MΩ, for example) and a feedback capacitor is relatively large (such as 5-10 μf, for example). An RC time constant, formed by the input resistor and feedback capacitor determine the charge rate of the feedback capacitor.

As is well known in the electronics art, a charge-transfer circuit, such as the combination of SW1 and C8, has a high effective resistance when controlled by a low frequency signal, such as the low frequency $S_{CLK}$ pulses, and a low effective resistance when controlled by a high frequency signal, such as the high frequency $S_{CLK}$ pulses. In accordance with the preferred embodiment of the invention, the switched-capacitor integrator 76 is selected so that the high effective resistance of SW1 and C8 is approximately 50 MΩ, the low effective resistance is approximately 50 KΩ, and the feedback capacitor (i.e., C7) is approximately 0.15 μf. As a result, when SW1 is clocked by low frequency $S_{CLK}$ pulses, the RC time constant of the switched-capacitor integrator 76 is approximately the same as the RC integrator used in the prior art, and hence, C7 charges at approximately the same rate as in the prior art. Thus, when a low DC offset is detected, the DC restoration circuit 66 does not act any quicker than the prior art in restoring $V_{E1}$ to a nominal value. However, for high frequency $S_{CLK}$ pulses, the RC time constant of the switched capacitor integrator 76 is much smaller than in the prior art and, as a result, C7 charges more rapidly. Since C7 charges more rapidly, the DC restoration circuit 66 restores the $V_{E1}$ voltage to a nominal value more rapidly than the prior art. Thus, when an excessive DC offset in the $V_{E1}$ voltage is detected, the DC restoration circuit 66 restores $V_{E1}$ to a nominal value faster than prior art methods. Furthermore, the smaller feedback capacitor (i.e., C7) permits further miniaturization of the apparatus 10.

As can be readily appreciated from the foregoing discussion, a method and apparatus is provided for use with a multiple ECG lead system that produces lead and transthoracic impedance information so that downstream devices may determine whether a leads-off condition exists and the pulmonary activity of a patient. Furthermore, the apparatus provides faster DC restoration and reduced size over conventional apparatus found in the prior art. While a preferred embodiment, and several illustrative examples of the invention have been described herein, it is to be understood that, within the scope of the appended claims, various changes can be made. For example, the frequencies of the $S_{LI}$ and $S_{IR}$ carrier signals can be different as can the values of $Z_1$, $Z_2$, $Z_3$ and $Z_4$. Also, other ECG lead configurations not discussed may be equally applied to the invention. Hence, the invention can be practiced other than as specifically described herein.

The embodiments of the invention in which an exclusive property or privilege is claimed are defined as follows:

1. An apparatus for use with medical diagnostic and therapeutic apparatus employing electrodes attached to a patient's skin for sensing the integrity of lead connections and patient transthoracic impedance comprising:
   (a) a carrier signal source means coupled to a first lead having a first lead impedance and coupled to a plurality of second leads having a plurality of second lead impedances:
      (i) for producing a first carrier signal having a lead impedance frequency component and an impedance respiration frequency component and for applying said first carrier signal to said first lead; and,
      (ii) for producing a second carrier signal having said lead impedance frequency component and said impedance respiration frequency component and for applying said second carrier signal to said plurality of second leads;
   (b) a receiver means coupled to said first lead and said plurality of second leads for receiving:
      (i) a first lead voltage produced by said first carrier signal and said first lead impedance; and, (ii) a plurality of second lead voltages produced by said second carrier signal and said plurality of second lead impedances;

(c) amplifying means, coupled to receive a plurality of combinations of said first lead voltage with one of said plurality of second lead voltages, for amplifying the difference between said first and second lead voltages in each of said combinations and producing;

(i) a plurality of first stage output voltages, one of said first stage output voltages being produced for each of said combinations of said first and second lead voltages; and, (ii) a plurality of second stage output voltages, one of said second stage output voltages being produced for each of said combinations of said first and second lead voltages; and, (d) a signal separator means coupled to said amplifying means for receiving said plurality of first stage output voltages and for producing:

(i) a plurality of lead impedance-related voltages related to said lead impedance frequency component of said first and second carrier signals; and, (ii) at least one impedance respiration-related voltages related to said impedance respiration frequency component of said first and second carrier signals.

2. The apparatus for sensing the integrity of lead connections and patient transthoracic impedance claimed in claim 1, wherein said first carrier signal is out of phase with said second carrier signal.

3. The apparatus for sensing the integrity of lead connections and patient transthoracic impedance claimed in claim 1, wherein said carrier signal source means comprises a terminating impedance network, said carrier signal source means applying said first and second carrier signals to said first lead and said plurality of second leads through said terminating impedance network.

4. The apparatus for sensing the integrity of lead connections and patient transthoracic impedance claimed in claim 3, wherein said terminating impedance network comprises:

(a) a first terminating impedance coupled to said first lead, wherein said carrier signal source means applies said first carrier signal to said lead through said first terminating impedance; and, (b) a plurality of second terminating impedances coupled to said plurality of second leads, wherein said carrier signal source means applies said second carrier signal to said plurality of second leads through said plurality of second terminating impedances.

5. The apparatus for sensing the integrity of lead connections and patient transthoracic impedance claimed in claim 4, wherein said first terminating impedance and said plurality of second terminating impedances have the same impedance values.

6. The apparatus for sensing the integrity of lead connections and patient transthoracic impedance claimed in claim 1, wherein said amplifying means includes one or more DC restoration circuits each coupled to receive one of said plurality of second stage output voltages, said DC restoration circuit producing an output that compensates for a DC offset in said one of said plurality of second stage output voltages.

7. The apparatus for sensing the integrity of lead connections and patient transthoracic impedance claimed in claim 6, wherein each said DC restoration circuit comprises a switched capacitor integrator.

8. The apparatus for sensing the integrity of lead connections and patient transthoracic impedance claimed in claim 1, wherein said signal separator means comprises:

(a) a plurality of lead impedance demodulators coupled to receive said plurality of first stage output voltages and produce said plurality of lead impedance-related voltages;

(b) at least one impedance respiration demodulator coupled to receive said plurality of said first stage output voltages and produce at least one transthoracic impedance-related voltage and, (c) at least one DC restoration circuit coupled to receive said at least one transthoracic impedance-related voltage, each of said at least one DC restoration circuit producing an output that compensates for a DC offset in said at least one impedance respiration-related voltage.

9. The apparatus for sensing the integrity of lead connections and patient transthoracic impedance claimed in claim 8, wherein said at least one DC restoration circuit comprises a switched-capacitor integrator.

10. The apparatus for sensing the integrity of lead connections and patient transthoracic impedance claimed in claim 8, wherein said plurality of lead impedance demodulators are clocked by a first control signal having a frequency equal to the frequency of said lead impedance component of said first and second carrier signals, and said at least one impedance respiration demodulator is clocked by a control signal having a frequency equal to the frequency of said impedance respiration component of said first and second carrier signals.

11. The apparatus for sensing the integrity of lead connections and patient transthoracic impedance claimed in claim 1, wherein said lead impedance frequency component has a frequency of 1024 Hz and said impedance respiration frequency component has a frequency of 18.432 kHz.

12. A method for sensing the integrity of lead connections and patient transthoracic impedance comprising the steps of:

(a) producing a first carrier signal having a lead impedance frequency component and an impedance respiration frequency component, and producing a second carrier signal having said lead impedance frequency component and said impedance respiration frequency component, wherein said first carrier signal is out of phase with said second carrier signal;

(b) applying said first carrier signal to a first lead having a first lead impedance and applying said second carrier signal to a plurality of second leads having a plurality of second lead impedances;

(c) receiving a first lead voltage produced by said first carrier signal and said first lead impedance and receiving a plurality of second lead voltages produced by said second carrier signal and said plurality of second lead impedances;

(d) amplifying the difference of a plurality of combinations of said first lead voltage and one of said plurality of second lead voltages and producing a plurality of first stage output voltages and a plurality of second stage output voltages; and, (e) producing a plurality of lead impedance-related voltages and at least one impedance respiration-related voltage from said plurality of first stage output voltages.

13. The method for sensing the integrity of lead connections and patient transthoracic impedance claimed in claim 12, wherein said step of producing said first and second carrier signals include the step of inverting one of said carrier signals.

14. The method of sensing the integrity of lead connections and patient transthoracic impedance claimed in claim 12, wherein said step of applying said first and second carrier signals to said first and said plurality of second leads comprises the step of passing said first and second carrier signals through a terminating impedance network.

15. The method for sensing the integrity of lead connections and patient transthoracic impedance claimed in claim 12, wherein said step of amplifying comprises the steps of:
(a) high pass filtering said plurality of first stage output voltages; and,
(b) restoring said plurality of second stage output voltages to nominal values by compensating for a DC offset in said plurality of second stage output voltages.

16. The method for sensing the integrity of lead connections and patient transthoracic impedance claimed in claim 15, wherein said step of restoring said plurality of second stage output voltages to nominal values includes the step of using one or more switched-capacitor integrators.

17. The method of sensing the integrity of lead connections and patient transthoracic impedance claimed in claim 12, wherein said step of producing a plurality of lead impedance-related voltages and at least one impedance respiration-related voltage comprises the steps of:
(a) demodulating said first stage output voltages at a frequency equal to the frequency of said lead impedance frequency component and producing said plurality of lead impedance-related voltages;
(b) demodulating at least one of said second stage output voltages at a frequency equal to said impedance respiration frequency component and producing said at least one impedance respiration-related voltage; and,
(c) restoring said at least one impedance respiration-related voltage to a nominal value by compensating for a DC offset in said at least one impedance respiration-related voltages.

18. The method for sensing the integrity of lead connections and patient transthoracic impedance claimed in claim 17, wherein said step of restoring said at least one impedance respiration-related voltage to a nominal value includes the step of using one or more switched-capacitor integrators.

* * * * *

UNITED STATES PATENT AND TRADEMARK OFFICE
CERTIFICATE OF CORRECTION

PATENT NO. : 4,919,145
DATED : April 24, 1990
INVENTOR(S) : Arthur R. Marriott It is certified that error appears in the above-identified patent and that said Letters Patent is hereby corrected as shown below:

| Column | Line | |
|---|---|---|
| 2 | 33 | "with" should be --without-- (2nd Occur.) |
| 4 | 2 | "to" should be --on-- |
| 7 | 7 | "above," should be --above.-- |
| 7 | 7 | "$Z_T1$" should be --$Z_T$-- |
| 7 | 47 | "are" should be --and-- |
| 10 | 26 | "capable" should be --cable-- |
| 10 | 28 | Delete the word "in" before the word "which" |
| 12 | 32 | "volage" should be --voltage-- |
| 12 | 33 | Insert the words --to determine-- after the word "invention" |
| 12 | 46 | Delete the phrase ", for example" (second occurrence) |
| 15 | 24, 25 | "voltages" should be --voltage-- |
| 15 | 46 | Insert the word --first-- before "lead" |
| 17 | 6 | "include" should be --includes-- |
| 18 | 3 | "of" should be --for-- (first occurrence) |
| 18 | 20 | "voltages" should be --voltage-- |

Signed and Sealed this

Ninth Day of February, 1993

*Attest:*

STEPHEN G. KUNIN

*Attesting Officer*      Acting Commissioner of Patents and Trademarks